(12) United States Patent
Moore

(10) Patent No.: US 11,497,742 B1
(45) Date of Patent: Nov. 15, 2022

(54) PHARMACEUTICAL COMPOSITION FOR THE TREATMENT OF COVID-19 INFECTION

(71) Applicant: Timothy S. Moore, Newtown, CT (US)

(72) Inventor: Timothy S. Moore, Newtown, CT (US)

( * ) Notice: Subject to any disclaimer, the term of this patent is extended or adjusted under 35 U.S.C. 154(b) by 0 days.

(21) Appl. No.: 17/515,322

(22) Filed: Oct. 29, 2021

(51) Int. Cl.
*A61K 31/4706* (2006.01)
*A61K 31/197* (2006.01)
*A61K 9/24* (2006.01)

(52) U.S. Cl.
CPC .......... *A61K 31/4706* (2013.01); *A61K 9/209* (2013.01); *A61K 31/197* (2013.01)

(58) Field of Classification Search
None
See application file for complete search history.

(56) References Cited

U.S. PATENT DOCUMENTS

| | | | | |
|---|---|---|---|---|
| 10,987,329 B1 * | 4/2021 | Raju | ................ | A61K 36/9066 |
| 2004/0214860 A1 * | 10/2004 | Charous | ............ | A61K 31/4706 |
| | | | | 514/312 |

OTHER PUBLICATIONS

Sanders, James M., et al. "Pharmacologic treatments for coronavirus disease 2019 (COVID-19): a review." JAMA 323.18 (2020): 1824-1836. (Year: 2020).*
Awad, Atheer, et al. Chapter 20—Liquid dosage forms, Editor(s): Adeboye Adejare, Remington (Twenty-third Edition), Academic Press, available online Nov. 13, 2020, pp. 359-379, https://doi.org/10.1016/B978-0-12-820007-0.00020-9. (Year: 2020).*
Gaisford, Simon. Chapter 17—Salt Selection, Editor(s): Adeboye Adejare, Remington (Twenty-third Edition), Academic Press, available online Nov. 13, 2020, pp. 307-314, https://doi.org/10.1016/B978-0-12-820007-0.00017-9. (Year: 2020).*
Kibbe, AH. "Ascorbic Acid." in Handbook of Pharmaceutical Excipients, Sixth Edition (2009) pp. 43-46. (Year: 2009).*

* cited by examiner

*Primary Examiner* — Bethany P Barham
*Assistant Examiner* — Peter Anthopolos
(74) *Attorney, Agent, or Firm* — Withers Bergman

(57) ABSTRACT

A bilayer composition for amelioration of, or prophylaxis against, SARS-CoV-2 infection comprising a: (i) a first layer consisting of 250 mg to 1600 mg of 5-aminolevulinic acid (ALA), or salt thereof, and pharmaceutically acceptable excipients that allow for immediate release of the 5-aminolevulinic acid; (ii) a second layer consisting of hydroxychloroquine (HCQ), and/or a salt thereof, in a dose of 100 mg-1500 mg, or salt thereof, and at least one pharmaceutically acceptable excipient comprising a release modifier for sustained release of the hydroxychloroquine or chloroquine.

20 Claims, No Drawings

PHARMACEUTICAL COMPOSITION FOR THE TREATMENT OF COVID-19 INFECTION

CROSS REFERENCE TO RELATED APPLICATIONS

The present application does not claim priority to an earlier application.

TECHNICAL FIELD

The present invention relates to stable pharmaceutical combination comprising hydroxychloroquine and/or chloroquine and/or a salt thereof and 5-aminolevulinic acid, or a salt thereof, for the treatment of Covid-19 infections.

BACKGROUND

A coronavirus, designated SARS-CoV-2, has caused widespread disruption throughout the world since 2019. Among the symptoms associated with SARS-CoV-2 infection is severe acute respiratory syndrome. This respiratory syndrome is also referenced as "Novel coronavirus-induced pneumonia." Besides respiratory issues, it has been found that SARS-CoV-2 infection is associated with other serious life-threatening sequelae including blood clotting disorders that can lead to strokes.

Coronavirus may directly penetrate the human cell membrane by way of porphyrin. Conserved domain analysis, homology modeling, and molecular docking employing NCBI protein sequences indicates that ORF8 and surface glycoprotein can bind to porphyrin. At the same time, orflab, ORF10, and ORF3a proteins are seen to be able to coordinate to attack the heme on the 1-beta chain of hemoglobin to dissociate the iron to form porphyrin. There appears to be a massive demand of porphyrins for viruses to survive. The novel coronavirus is hypothesized to target hemoglobin and attack heme possibly directly interfering with the assembly of human hemoglobin. Thus, a characteristic of SARS-CoV-2 infection is porphyrin excess which may interfere with the normal heme anabolic pathway.

Most efforts to treat SARS-CoV-2 infection have been directed to reduce RNAemia (viral load reduction). Initial attempts used broad-spectrum antiviral drugs like nucleoside analogues and HIV-protease inhibitors, such as lopinavir-ritonavir, remdesivir, favipiravir, ribavirin and galidesivir. Such were not been found to be very effective in interfering with the immune evasion of SARS-CoV-2. Recently Merck and Ridgeback have advanced an investigation oral antiviral known as Molnupiravir (MK-4482/EIDD-2801) a potent ribonucleoside analog. Merck has reported that based on an interim analysis the drug reduced the risk of hospitalization or death by approximately 50%. However, such analysis was based on only 775 patients (albeit an emergency use authorization is being sought for its administration).

Some have hypothesized that many of the symptoms associated with SARS-CoV-2 infection may be the sequalae of acute *porphyria* caused by the viruses attack on hemoglobin. It is known that excess porphyrins in red blood cells can lead to hemolytic anemia and can causes cell lysis.

Contra to the acute *porphyria* sequelae hypothesis, the present inventor notes that U.S. Pat. No. 11,026,909 discloses 5-aminolevulinic acid to be therapeutically useful in the therapy of Covid-19 patients. 5-aminolevulinic acid ("5-ALA") is a precursor of protoporphyrin IX that is ultimately converted to heme. Thus, the inventor recognized that the administration of 5-ALA would be expected to increase porphyrin production given the bioavailability disclosed in U.S. Pat. No. 11,026,909. 5-Aminolevulinic acid (5-ALA) may be administered in one of its salts, including the HCl, and phosphate salts.

The present inventor understood that the usefulness of 5-ALA argues against the acute *porphyria* hypothesis for a predominate mechanism for symptoms associated with SARS-CoV-2 infection.

Much interest has been raised in regard to the drugs hydroxychloroquine and chloroquine in the treatment of SARS-CoV-2 infection. Fantini et al., *Structural and molecular modelling studies reveal a new mechanism of action of chloroquine and hydroxychloroquine against SARS-CoV-2 infection*, Intern. J. Antimicrobial Agents 55(5): May 2020, based on structural and molecular modelling studies which suggest that the drugs interfere with the viral S protein to make it no longer able to bind the ganglioside-binding domain at the tip of the N-terminal domain of the SARS-CoV-2 protein. Molecular studies by Hussein and Elkhair, *Molecular docking identification for the efficacy of some zinc complexes with chloroquine and hydroxychloroquine against main protease of Covid*-19, J. Mol. Struct. 1231, 129979 (May 5, 2021) indicate that the zinc complexes of chloroquine (CQ)/hydroxychloroquine (HCQ) may provide enhanced activity against SARS-CoV-2 due to low binding energies. In particular, these authors found $Zn(CQ)Cl_2H_2O)$ and $Zn(HCQ)Cl_2H_2O$ as potent inhibitors for COVID-19 Mpro.

The present inventor has recognized that beyond a potential blocking effect of chloroquine and hydroxychloroquine with sites associated with the SAR-COV-2 protein to inhibit interaction with cell receptor sites, that choroquine and hydroxychloroquine also release tissue-bound porphyrins, and lead to its rapid elimination. Scholnick Pl, et al. The *Molecular Basis of the Action of Chloroquine in Porphyria Cutanea Tarda*, J. Invest. Dermatology, 61(4):226-232 (1973).

Undoubtedly, porphyrin is an important material for the synthesis of heme. 5-ALA would be expected, if anything, to enhance porphyrin production. 5-ALA is assembled into heme in the mitochondria. As a dipeptide it can pass through dipeptide transporters on the cell surface. The present inventor recognized that the disclosure of U.S. Pat. No. 11,026,909 of the usefulness of 5-ALA in SARS-CoV-2 infections suggests that it is not too much porphyrin that is the problem in SARS-CoV-2 infections, rather, as set forth in U.S. Pat. No. 11,026,909, that the virus is attacking heme leading to too much free iron in the body. That is, the virus competes with iron for the porphyrin. Thus, many of the symptoms seen in Covid-19 infections may actually be due to toxic oxidative iron that is disassociated by the virus rather than acute *porphyria*.

The present inventor has recognized that it is porphyrin production and elimination that must be balanced to effectively treat the symptoms of SARS-CoV-2 infection to reduce iron toxicity. The present inventor has recognized that a combination of CQ, HCQ, and salts therein with 5-aminolevulinic acid, and salts thereof, provides an improved palliative to prevent the serious sequelae associated with Covid-19, particularly severe Covid-19. They have understood that such combination optimizes porphyrin in the blood of patients suffering from Covid-19 to prevent too much free iron from circulating in the blood without causing significant symptoms associated with acute *porphyria*. That is, they have discovered that via the co-administration of 5-aminolevulinic acid and ivermectin, one can effectuate a balance between the need for porphyrin due to the SARS-CoV-2 virus interference with porphyrin to remove the iron from hemoglobin, the excess free iron in the blood caused by SARS-CoV-2 infection, and the release of porphyrin from the cells.

The present inventor has recognized that a combination of hydroxychloroquine, chloroquine, and zinc complex salts thereof with 5-aminolevulinic acid provides an improved palliative to prevent the serious sequelae associated with Covid-19, particularly severe Covid-19. They have understood that such combination optimizes porphyrin in the blood of patients suffering from Covid-19 to prevent too much free iron from circulating in the blood without causing significant symptoms associated with acute *porphyria*. That is, they have discovered that via the co-administration of 5-aminolevulinic acid (and salts thereof) and hydroxychloroquine, chloroquine, and zinc complexes thereof, one can effectuate a balance between the need for porphyrin due to the SARS-CoV-2 virus interference with porphyrin to remove the iron from hemoglobin, the excess free iron in the blood caused by SARS-CoV-2 infection, and the elimination of porphyrin from the body.

In designing a dosage form containing both 5-aminolevulinic acid and CQ, HCQ, and zinc salts thereof, the present inventor also has determined that the optimal use of the compounds in a single administrable pharmaceutical optimally requires that the compounds be separated from one another in time of administration. The inventor has recognized that the uptake of 5-ALA, into mitochondria is interfered with by concomitant hydroxychloroquine and chloroquine administration (and salts thereof). Thus they propose a pharmaceutical dosage form wherein the 5-ALA is found in an immediate release component, while the CQ, HCQ, and salts thereof (particularly zinc salts), are associated with a delayed released component. They also propose propose a pharmaceutical dosage form wherein the CQ, HCQ, and salts thereof (particularly zinc salts) is found in an immediate release component, while the 5-ALA salts thereof (particularly zinc salts), are associated with a delayed released component.

SUMMARY OF THE INVENTION

Accordingly, the invention herein provides therapeutic combinations advantageous for the treatment of SARS-CoV-2 infections comprising 5-ALA, or salts thereof, and CQ, HCQ, or salts thereof (particularly zinc salts thereof, Such combination includes a stable bilayer tablet composition having a first layer consisting of consisting of 250 mg-1600 mg of 5-aminolevulinic acid, or a salt thereof, and a second layer containing enterically coated sustained release layer comprising CQ, and/or HCQ, and/or a salt thereof, in a dose of 100 mg-1500 mg.

BRIEF DESCRIPTION OF THE INVENTION

The term "composition" as used herein refers to a dosage form suitable for oral administration, such as tablets, granules, powder, spheroids, pellets, pills, capsule, solution, suspension, emulsion and the like.

The term "bilayer tablet" as used herein refers to a coated or uncoated tablet with two layers of different materials compressed together wherein each layer having same or different release profiles.

The term "pharmaceutically acceptable" as used herein means that which is useful in preparing a pharmaceutical composition that is generally safe and non-toxic.

The term "excipients" as used herein means a component of a pharmaceutical product that is not an active ingredient such as, for example, diluents, binders, carriers and the like. The excipients that are useful in preparing a pharmaceutical composition are generally safe and non-toxic.

Suitable fillers include, but are not limited to starch, dibasic calcium phosphate, tribasic calcium phosphate, cellulose derivatives, microcrystalline cellulose or wood cellulose (including microcrystalline cellulose 302), calcium carbonate, dextrose, kaolin, magnesium carbonate, magnesium oxide, lactose monohydrate, sugar alcohols such as mannitol, sorbitol, erythritol and the like and combinations thereof lactose, lactose anhydrous, sucrose, starch, pregelatinized starch, dextrose, mannitol (including mannitol Pearlitol SD 200), fructose, xylitol, sorbitol, corn starch, modified corn starch, inorganic salts such as calcium carbonate, calcium phosphate, dicalcium phosphate, calcium sulfate, dextrin/dextrates, maltodextrin, compressible sugars, and other known bulking agents or fillers, and/or mixtures of two or more thereof. Preferred fillers are microcrystalline cellulose, lactose monohydrate, mannitol and combinations thereof. Several types of microcrystalline cellulose are suitable for use in the formulations described herein, for example, microcrystalline cellulose selected from the group consisting of Avicel® types: PH101, PH102, PH103, PH105, PH 112, PH113, PH200, PH301, and other types of microcrystalline cellulose, such as silicified microcrystalline cellulose. Several types of lactose are suitable for use in the formulations described herein, for example, lactose selected from the group consisting of anhydrous lactose, lactose monohydrate, lactose fast flo, directly compressible anhydrous lactose, and modified lactose monohydrate Suitable binders include, but are not limited to carbomers, dextrin, corn starch, modified corn starch, ethyl cellulose, carboxymethyl cellulose (including sodium carboxymethyl cellulose), hydroxypropyl cellulose (including hydroxypropyl cellulose EXF), hydroxypropyl methylcellulose (HPMC) (including hydroxypropyl methylcellulose 2208), povidone, copovidone, polyvinyl pyrrolidone (PVP), gelatin, polymethacrylates, pregelatinized starch, sodium alginate, gums, synthetic resins, silicic acid and the like and combinations thereof. lactose, gum acacia, ethyl cellulose, cellulose acetate, as well as a wax binder such as carnauba wax, paraffin, spermaceti, polyethylenes or microcrystalline wax, as well as other conventional binding agents and/or mixtures of two or more thereof.

Suitable disintegrants include, but are not limited to croscarmellose sodium, sodium starch glycolate, crospovidone, polacrillin potassium, microcrystalline cellulose, carboxymethyl cellulose calcium, starches such as corn starch, potato starch, pre-gelatinized starch and modified starches, clays, bentonite, and the like and combinations thereof. Preferred disintegrants are croscarmellose sodium, corn starch and combinations thereof microcrystalline cellulose, low substituted hydroxypropyl cellulose and other known disintegrants. Several specific types of disintegrant are suitable for use in the formulations described herein. For example, any grade of crospovidone can be used, including for example crospovidone XL-10, and includes members selected from the group consisting of Kollidon CL®, Polyplasdone XL®, Kollidon CL-M®, Polyplasdone XL-10®, and Polyplasdone INF-10®. In one embodiment, the disintegrant, if present, of the stock granulation is sodium starch glycolate, croscarmellose sodium and/or crospovidone.

Suitable lubricants include, but are not limited to calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulfate, sodium stearyl fumarate, stearic acid, talc, calcium stearate, talc, carnauba wax, stearic acid, palmitic acid, zinc stearate, myristic acid, and hydrogenated vegetable oils and fats, and the like and combinations thereof. Preferred lubricant is magnesium stearate.

Suitable glidants include, but are not limited to colloidal silicon dioxide (and other forms of silicon dioxide), such as aggregated silicates and hydrated silica, talc, starch, starch derivatives, colloidal silicon dioxide, magnesium silicate, magnesium trisilicate, and the like and combinations thereof. Preferred glidant is colloidal silicon dioxide.

Examples of suitable release modifiers include, but are not limited to, hydroxypropyl methylcellulose, polyvinyl alcohol (PVA), ethyl cellulose, methacrylic polymers, hydroxypropyl cellulose, starches, gums, cellulose ethers, protein derived materials, nylon, acrylic resins, polylactic acid, polyvinylchloride, vinyl acetate/vinyl chloride copolymers, acrylonitrile/vinylidene chloride copolymers, polydimethylsiloxanes, copolymers derived from (meth) acrylic acid, ethyl acrylate and methylacrylate copolymers, ethylammonium methacrylate and methyl acrylate copolymers, ethylammonium methacrylate and methyl methacrylate copolymers, ethylammonium methacrylate and ethyl acrylate copolymers, ethylammonium methacrylate and methyl methacrylate copolymers, methacrylic acid and ethyl acrylate copolymers, methacrylic acid and methyl methacrylate copolymers, polyvinylpyrrolidones, and cellulose acetate phthalate.

Provided herein is a bilayer composition for amelioration of, or prophylaxis against, SARS-CoV-2 infection comprising a: (i) a first layer consisting of 250 mg to 1600 mg of 5-aminolevulinic acid (ALA), or salt thereof, and pharmaceutically acceptable excipients that allow for immediate release of the 5-aminolevulinic acid; (ii) a second layer consisting of hydroxychloroquine (HCQ), and/or a salt thereof, in a dose of 100 mg-1500 mg, or salt thereof, and at least one pharmaceutically acceptable excipient comprising a release modifier for sustained release of the hydroxychloroquine or chloroquine.

The composition may comprise a tablet, a capsule or other pharmaceutical composition.

In an embodiment, the present invention provides a stable bilayer tablet composition comprising 5-aminolevulinic acid or a salt thereof, and CQ and/or HCQ, or salt thereof, and pharmaceutically acceptable excipients comprising one or more of fillers, binders, disintegrants, lubricants, glidants and the like.

In a embodiment the bilayer tablet comprises: (i) a first layer consisting of 250 mg to 1600 mg of 5-aminolevulinic acid (ALA), or salt thereof, and pharmaceutically acceptable excipients that allow for immediate release of the 5-aminolevulinic acid; and (ii) a second layer consisting of hydroxychloroquine (HCQ) or chloroqune (CQ), and/or a salt thereof, in a dose of 100 mg-1500 mg, and at least one pharmaceutically acceptable excipient comprising a release modifier for sustained release of the hydroxychloroquine and or chloroquine.

In a preferred embodiment the 5-aminolevulinic acid is in a zinc salt form. The zinc salt may be zinc-aminolevulinic acid or $Zn(ALA)_2$. In another preferred embodiment, the hydroxychloroquine salt is $Zn(HCQ)Cl_2H_2O$. A preferred chloroquine salt may be $Zn(CQ)Cl_2H_2O$.

When made into a tablet, the tablet may be in the form of a caplet. The tablet may be coated with a film coating, that may be enteric in nature, that is a polymer that serves as a barrier to prevent the gastric acids in the stomach from dissolving or degrading the active after swallowing the same.

The CQ, or HCQ XR layer (1000 mg) comprises CQ or HCQ, or a salt thereof, binder, release modifier, lubricant, and optionally glidant. A preferred binder is sodium carboxymethyl cellulose. Hydroxypropyl methylcellulose 2208 is a preferred release modifier. Magnesium stearate is a preferred lubricant and silicon dioxide or colloidal silicon dioxide are preferred glidants.

The 5-ALA, or salt thereof, layer comprises 5-ALA, or salt thereof, filler, disintegrant, glidant, and lubricant. Among preferred fillers are lactose anhydrous, microcrystalline cellulose 302, pregelatinized starch, and mannitol. A preferred disintegrant is crospovidone. Silicon dioxide is the preferred glidant and magnesium stearate is a preferred lubricant. Hydroxypropyl cellulose EXF is a preferred binder.

Thus the present invention provides bilayer compositions comprising (1) a CQ, HQ, or salt thereof, XR formulation as the second layer, (2) a 5-ALA, or salt thereof, formulation as the first layer covering the second layer, and (3) optionally a film coating that covers both layers. CQ, HQ may be in the form of a pharmaceutically acceptable salt such as HQ sulfate or a zinc salt such as $Zn(CQ)Cl_2H_2O$) and $Zn(HCQ)Cl_2H_2O$. The 5-ALA salt may be the HCl, and/or phosphate salts, or $Zn(ALA)_2$ and/or zinc-aminolevulinic acid, or a mixture thereof.

The 5-ALA layer may be immediate release or an extended-release formulation (wherein, e.g., a suitable release modifier is added to the layer), but an immediate release formulation is preferred.

In one embodiment there is provided a bilayer tablet comprising: (1) a first layer wherein the first layer comprises 5-ALA, or a salt thereof, comprising about 20-30% of 5-ALA, or salt thereof, about 5-30% lactose anhydrous, about 40-90% microcrystalline cellulose, about 0-25% pregelatinized starch, about 0-20% hydroxypropyl cellulose, about 0-25% mannitol, about 1-10% crospovidone, about 0.1-5% silicon dioxide, and about 0.1-5% magnesium stearate, in which weight percents are calculated relative to the total weight of the first layer (2) a second layer CQ, HCQ, or salt thereof, comprising about 50-87% CQ, HCQ, or salt thereof, about 1-10% sodium carboxymethyl cellulose, about 10-40% hydroxypropyl methylcellulose, about 0.1-75% magnesium stearate, and about 0-2% silicon dioxide or about 0-1.5% colloidal silicon dioxide in an total amount of 500 mg, in which weight percents are calculated relative to the total weight of the second layer; and (3) optionally a film coating that covers the first layer and the second layer, wherein the weight ratio between the first layer and the second layer may be about 3:4.

The therapeutic combination as disclosed herein advantageously achieves a therapeutic synergy in treating the Covid-19 in the patient/subject.

The compositions are prepared by techniques known by the skilled person in the art like direct compression or wet granulation or dry granulation.

Direct compression technique generally involves blending all ingredients in a blender for suitable time till to achieve blend uniformity and compressing into tablets of suitable size and shape.

Wet granulation technique generally involves utilization of solvents for preparation of granules. This process generally has the steps of mixing active ingredient with diluent, optionally disintegrant, granulating this mixture either by aqueous or non-aqueous granulation, drying the granulate, optionality sieving dried granules and blending dried granules with optionally further diluent, disintegrant, optionally sweetening agent, optionally flavoring agent, optionally colorant and lubricated with lubricant. Suitable solvents used according to the present invention for preparation of wet granulation are selected from water, isopropyl alcohol, methylene chloride and combinations thereof.

Dry granulation is another technique which doesn't use any solvents for preparation of granules. This process generally has the steps of mixing active ingredient with diluent, optionally disintegrant, optionally lubricant, optionally glidant, slugging and de-slugging and blending with optionally diluent, optionally disintegrant, optionally lubricant, optionally glidant, optionally sweetening agent, optionally flavoring agent, optionally colorant.

EXAMPLE 1 (METHOD OF MANUFACTURE)

The bilayer tablet composition is prepared by making two separate granulations containing HCQ in one granulation and 5-ALA in the other granulation.

HCQ is combined with magnesium stearate, and sodium carboxymethyl cellulose and mixed in a high shear granulator. Purified water is added with stirring. The wet granulated material is passed through a mill and then dried until moisture content is 1.0% or less. The milled HCQ formulation is added to milled hyroxypropyl methylcellulose 2208 USP and magnesium stearate added.

The 5-ALA granulation is performed by blending 5-ALA with microcrystalline cellulose, anhydrous lactose, a portion of crospovidone, and a portion of silicon dioxide in a tumble mixer and passed through a suitable conical mill. Magnesium stearate (screened) is blended into the mixture and then compacted using a roller compactor. The granules are blended with the remaining amount of crospovidone and silicon dioxide in a suitable tumble mixer.

A bilayer tablet press is used with the 5-ALA granulation in one hopper and the HCQ granulation in a second hopper. Tablet press is set to obtain the target weight, for the first layer. The second hopper is then opened and the target weight of the tablet press adjusted to obtain the tablet weight desired. Once target weight is obtained, the press is adjusted to obtain the target hardness.

Preferably, the HCQ granulation is manufactured for extend-release, however, the 5-ALA granulation may also, or instead, be manufactured for extend-release.

EXAMPLE 2 (EXEMPLARY FORMULATION)

Bilayer tablet composition comprising 5-ALA and ivermectin, or salts thereof:

|  | Ingredients | % w/w mg/unit |
|---|---|---|
| First layer: | 5-ALA or salt thereof | 300.00 |
|  | Lactose Anhydrous | 96.00 |
|  | Microcrystalline cellulose 302 | 445.00 |
|  | Silicon dioxide | 9.00 |
|  | Crospovidour | 24.00 |
|  | Magnesium Stearate | 6.00 |
|  | Purified water | Qs |

-continued

|  | Ingredients | % w/w mg/unit |
|---|---|---|
| Total (immediate release layer): |  | 880.00 |
| Second Layer: | CQ or HCQ or salt thereof | 200.00 |
|  | Na Carboxymethyl Cellulose | 10.00 |
|  | Magnesium Stearate | 0.71 |
|  | Hydroxypropyl methylcellulose | 78.60 |
|  | Purified water | --- Qs |
| Total (extend layer): |  | 289.31 |
|  | Core tablet weight (First layer + Second layer) | 1169.31 |
|  | Film coating material weight -Opadry II | 40.31 |
|  | Total weight of coated tablet | 1209.62 |

While the invention has been described by reference to specific embodiments, this was done for purposes of illustration only and should not be construed to, limit the spirit or scope of the invention.

The invention claimed is:

1. A bilayer tablet comprising:
   (i) a first layer consisting of 250 mg to 1600 mg of 5-aminolevulinic acid (ALA), or salt thereof, and pharmaceutically acceptable excipients that allow for immediate release of the 5-aminolevulinic acid;
   (ii) a second layer consisting of hydroxychloroquine (HCQ), and/or a salt thereof, in a dose of 100 mg-1500 mg, or salt thereof, and at least one pharmaceutically acceptable release modifier for sustained release of the hydroxychloroquine.

2. The bilayer tablet of claim 1 wherein the 5-aminolevulinic acid is in a zinc salt form.

3. The bilayer tablet of claim 2 wherein the salt is zinc-aminolevulinic acid.

4. The bilayer tablet of claim 2 wherein the salt is $Zn(ALA)_2$.

5. The bilayer tablet of claim 2 wherein the hydroxychloroquine salt is $Zn(HCQ)Cl_2H_2O$.

6. The bilayer tablet of claim 5 wherein the 5-aminolevulinic acid salt is $Zn(ALA)_2$.

7. The bilayer tablet of claim 1 in the form of a caplet.

8. The bilayer tablet of claim 1 wherein the first and second layers are coated with a film coating.

9. The bilayer tablet of claim 8 wherein the film coating is an enteric coating.

10. The bilayer tablet of claim 1 wherein the pharmaceutically acceptable excipients that allow for immediate release of the 5-aminolevulinic acid includes microcrystalline cellulose.

11. A bilayer tablet comprising:
    (i) a first layer consisting of 250 mg to 1600 mg of 5-aminolevulinic acid (ALA), or salt thereof, and pharmaceutically acceptable excipients that allow for immediate release of the 5-aminolevulinic acid;
    (ii) a second layer consisting of chloroquine (CQ), and/or a salt thereof, in a dose of 100 mg-1500 mg, or salt thereof, and at least one pharmaceutically acceptable release modifier for sustained release of the chloroquine.

12. The bilayer tablet of claim 11 wherein the 5-aminolevulinic acid is in a zinc salt form.

13. The bilayer tablet of claim 12 wherein the salt is zinc-aminolevulinic acid.

14. The bilayer tablet of claim 11 wherein the salt is $Zn(ALA)_2$.

15. The bilayer tablet of claim 11 wherein the hydroxychloroquine salt is $Zn(CQ)Cl_2H_2O$.

16. The bilayer tablet of claim 15 wherein the 5-aminolevulinic acid salt is $Zn(ALA)_2$.

17. The bilayer tablet of claim 11 in the form of a caplet.

18. The bilayer tablet of claim 11 wherein the first and second layers are coated with a film coating.

19. The bilayer tablet of claim 18 wherein the film coating is an enteric coating.

20. The bilayer tablet of claim 11 wherein the at least one pharmaceutically acceptable release modifier for sustained release of the hydroxychloroquine includes hydroxypropyl methylcellulose.

\* \* \* \* \*